United States Patent [19]

Okamoto et al.

[11] Patent Number: 5,535,614
[45] Date of Patent: Jul. 16, 1996

[54] THERMAL CONDUCTIVITY GAS SENSOR FOR MEASURING FUEL VAPOR CONTENT

[75] Inventors: Eiji Okamoto; Kuniaki Miyake, both of Fujisawa, Japan

[73] Assignee: NOK Corporation, Tokyo, Japan

[21] Appl. No.: 336,223

[22] Filed: Nov. 7, 1994

[30] Foreign Application Priority Data

Nov. 11, 1993 [JP] Japan ................................. 5-282725
Nov. 11, 1993 [JP] Japan ................................. 5-282729

[51] Int. Cl.$^6$ ................................................. G01N 27/18
[52] U.S. Cl. ..................... 73/23.31; 73/25.03; 73/25.05; 374/44; 338/22 R; 338/235; 338/229
[58] Field of Search ................................. 73/23.31, 23.32, 73/25.01, 25.03, 25.05; 374/44; 338/28, 22 R, 22 SP, 235, 236, 237, 234, 229

[56] References Cited

U.S. PATENT DOCUMENTS

| | | | |
|---|---|---|---|
| 3,616,677 | 11/1971 | Oppegaard | 73/25.03 X |
| 4,461,166 | 7/1984 | Gatten et al. | 73/25.03 |
| 4,720,421 | 1/1988 | Khilnani | 428/222 |
| 4,813,267 | 3/1989 | Norem et al. | 73/23.4 |
| 4,850,714 | 7/1989 | Wieglab | 374/44 |
| 4,902,138 | 2/1990 | Goeldner et al. | 374/44 |
| 4,944,035 | 7/1990 | Aagardl et al. | 73/25.03 X |
| 5,348,394 | 9/1994 | Hori et al. | 374/94 |

FOREIGN PATENT DOCUMENTS

| | | |
|---|---|---|
| 55-7698 | 1/1980 | Japan . |
| 57-16343 | 1/1982 | Japan . |
| 62-2438 | 1/1987 | Japan . |
| 62-170844 | 7/1987 | Japan . |
| 5-18055 | 3/1993 | Japan . |

*Primary Examiner*—Michael J. Brock
*Attorney, Agent, or Firm*—Jacobson, Price, Holman & Stern

[57] ABSTRACT

A gas sensor of the thermal conductivity type suitable for the quantitative analysis of the fuel vapor content of a fuel-air mixture. The gas sensor (10) comprises a sensing element (28) and a compensating element (30), each of which includes an electrically-heated hot member (38) incorporated into a Wheatstone bridge circuit powered by a constant current supply circuit (70). The constant current supply circuit (70) is adjusted and regulated such that the hot member (38) of the sensing element (28) is heated with an electric current of such an intensity that corresponds to a point of transition (Y) at which, at the interface of the hot member (38) and the mixture, the predominant mode of heat transfer changes from thermal conduction to natural convection.

5 Claims, 11 Drawing Sheets

THERMAL CONDUCTIVITY GAS SENSOR FOR MEASURING FUEL VAPOR CONTENT

BACKGROUND OF THE INVENTION

1. Field of the Invention

The present invention relates broadly to a gas sensor of the thermal conductivity type for use in the quantitative analysis of a gaseous mixture. More particularly, this invention is concerned with a gas sensor of the class mentioned which may suitably be used for measurement of fuel vapor content of a fuel-air mixture in an automotive emission control system.

2. Description of the Prior Art

Figure 1:
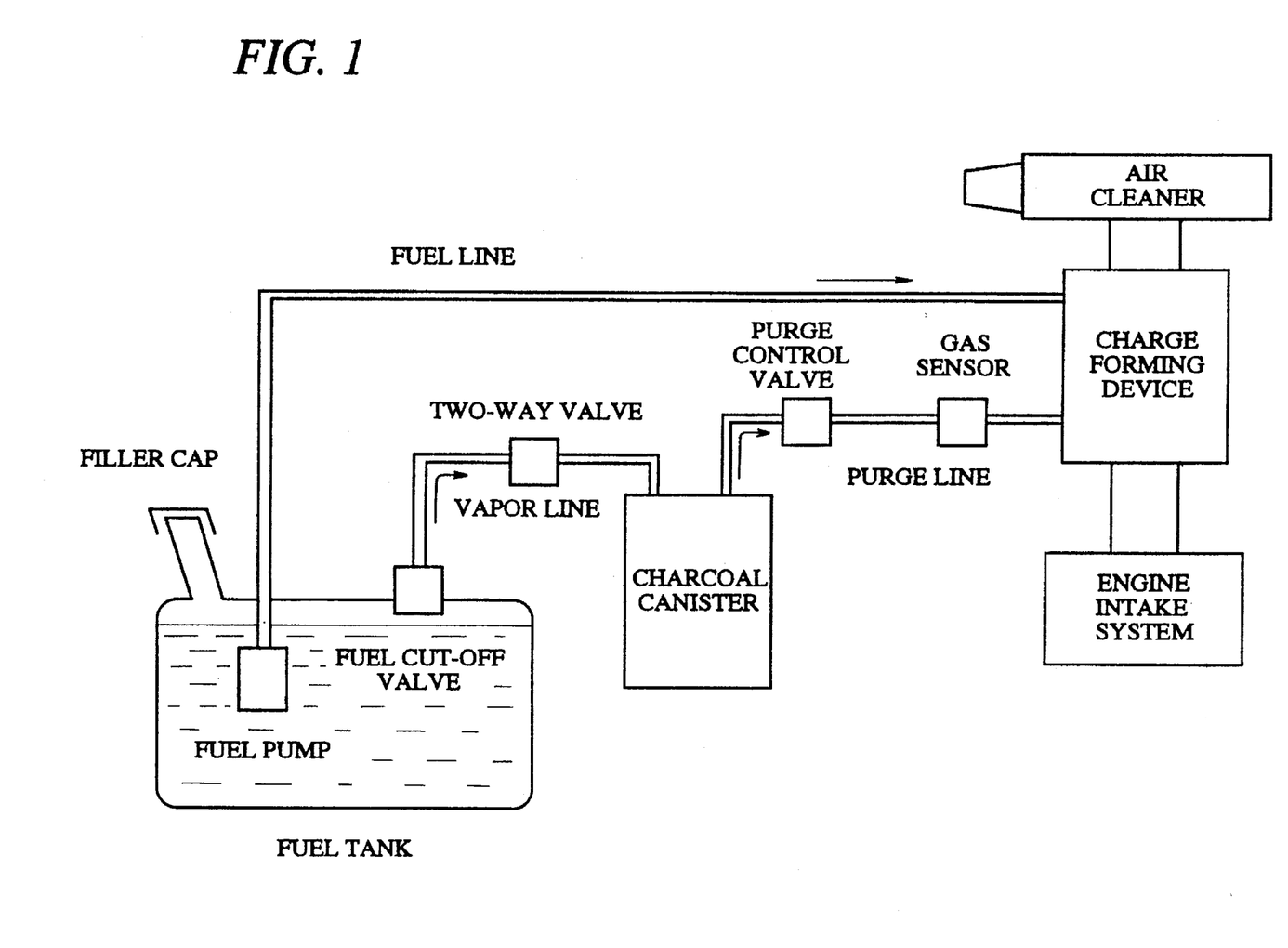
FIG. 1 is a schematic representation of an evaporative emission control system of automobiles.

Conventional evaporative emission control system of automobiles generally includes a charcoal canister connected to a fuel tank as schematically shown in FIG. 1. When the automotive engine is not running, fuel vapor generated in the fuel tank is forwarded via a fuel cut-off valve and a two-way valve to the canister for adsorption by activated charcoal. As the engine is restarted, a purge control valve in a purge line permits air to be drawn through the canister under the action of intake vacuum whereby fuel is desorbed and purged from the canister and is delivered to the engine intake system for combustion in the engine cylinders.

In order to reduce exhaust emissions as well as to achieve fuel economy, it is desirable that fuel from a fuel line be metered by a charge forming device, such as an electronically controlled fuel injection system, on account of the amount of fuel coming from the purge line. To this end, it is desirable to detect the amount of fuel flowing through the purge line. It is therefore contemplated to provide a gas sensor in the purge line in order to continuously monitor the fuel vapor content.

Known in the art are various types of gas sensors, including semiconductor type, catalytic combustion type and thermal conductivity type. Among them, gas sensors of the thermal conductivity type are known as being free from deterioration and contamination and being responsive to a wide range of gas composition.

Gas sensors of the thermal conductivity type are well-known known in the art as disclosed, for example, in U.S. Pat. No. 4,813,267 granted to Norem et al, Japanese Patent Kokai Publication Nos. 55-7698 and 57-16343, and Japanese Patent Kokoku Publication No. 5-18055. Gas sensors of the thermal conductivity type are designed to issue a voltage signal indicative of the composition of a two-components gas mixture by making use of the principle that any gas has an intrinsic thermal conductivity. Table 1 given below indicates intrinsic thermal conductivity of exemplary gases.

TABLE 1

(Thermal conductivity of gases at 300° K. under the standard atmospheric pressure)

| Gas Species | Thermal Conductivity (mW/m · K.) |
|---|---|
| hydrogen | 181 |
| helium | 153 |
| methane | 33.55 |
| oxygen | 26.29 |
| nitrogen | 25.98 |
| air | 26.14 |
| carbon monoxide | 24.87 |
| ammonia | 24.6 |

TABLE 1-continued (Thermal conductivity of gases at 300° K. under the standard atmospheric pressure)

| Gas Species | Thermal Conductivity (mW/m · K.) |
|---|---|
| ethylene | 20.5 |
| propane | 18.4 |
| carbon dioxide | 16.55 |
| isobutane | 16.3 |

As the thermal conductivity of a two-component gas mixture is proportional to the mixture ratio, the content of one component in the mixture can be derived once the thermal conductivity of the mixture is detected.

More specifically, a gas sensor of the thermal conductivity type typically includes a pair of elements which are generally identical in structure, size and thermal property with one another. Each element comprises an enclosure defining a chamber therein and serving as a heatsink. In each chamber, an electrically-heated hot member, such as a hot wire of platinum or a thermistor, having a temperature responsive electrical resistance is placed. The hot members of both elements are incorporated into a four-resistor Wheatstone bridge circuit and are heated by an electric current of controlled, constant intensity.

In use, the hot member of one element, known as the sensing element, is brought into contact with a gas mixture to be tested, with the hot member of the other element, known as the compensating element, being in contact with a reference gas. As both of the hot members are constantly energized by an electric current of a controlled predetermined intensity, a substantially equal amount of heat will be generated in each of the hot members. Given the velocity of gas to be zero so that heat transfer by way of the forced convection process does not occur, heat emanating from respective hot members will be transferred by way of the thermal conduction of surrounding gas to respective enclosures serving as heatsinks which are subjected to the ambient temperature. In a thermally equilibrated condition, the temperature of the hot member will be dependent on the thermal conductivity of gas surrounding the hot member.

Thus, in the compensating element, the temperature of the hot member will be constant since the heater is in contact with a reference gas which has a given thermal conductivity.

On the other hand, in the sensing element wherein the hot member is in contact with a gas mixture to be tested, any change in the composition of the mixture will result in a change in the thermal conductivity thereof. This brings about a change in the amount of heat transfer per unit time and, hence, a change in the hot member temperature which, in turn, results in a change in the electrical resistance thereof, so that an unbalanced voltage potential is developed across the output terminals of the Wheatstone bridge circuit.

The mixture ratio of a particular gas component in a two-component mixture may then be determined according to the difference between the output voltage developed with the mixture to be tested and the full-scale output voltage which would be developed with a pure gas consisting solely of the particular gas component of interest.

However, the problem associated with a gas sensor of the thermal conductivity type as applied to the measurement of the fuel vapor content in a fuel-air mixture is that the output voltage of the Wheatstone bridge is not always reliable. It has been observed that, when a mixture of a given fuel content is tested with the hot member being heated with varying current intensity, the output potential has fluctuated considerably. This makes the measurement of the fuel vapor content practically impossible.

Another problem which must be overcome in designing a commercially feasible gas sensor for use in an automotive emission control system is related to the pressure dependency of the output signal. Since the intake pressure of the engine varies significantly in response to varying operating conditions of the engine, the gas sensor is subjected to a wide range of pressure variation. Measuring errors which would result from intake pressure variation is non-negligible in properly controlling the fuel-to-air ratio of the combustible mixture.

SUMMARY OF THE INVENTION

Accordingly, an object of the present invention is to provide a gas sensor of the thermal conductivity type which is suitable for use with an automotive emission control system for the measurement of fuel vapor content of a fuel-air mixture.

Another object of the invention is to provide a gas sensor of the thermal conductivity type which has a high degree of reliability.

A still another object of the invention is to provide a gas sensor of the thermal conductivity type which is able to deliver an output signal having a small pressure dependency.

A further object of the invention is to provide a gas sensor of the thermal conductivity type which is adapted to issue a full-scale output signal of a high level.

Another object of the invention is to provide a gas sensor of the thermal conductivity type having an improved sensitivity.

According to the invention, these objects may be achieved by a gas sensor of the thermal conductivity type having a sensing element and a compensating element, each of which comprises an electrically-heated hot member incorporated into a Wheatstone bridge circuit powered by a constant current supply circuit.

The feature of the present invention is that the constant current supply circuit is adjusted and regulated such that the hot member of the sensing element is heated with an electric current of such an intensity that, at the interface of the hot member and the gas mixture to be tested, heat transfer from the hot member to the mixture takes place primarily in the thermal conduction mode.

This feature is based on the discovery that there is a certain correlation between the intensity of electric current fed to the hot member of the sensing element and the output voltage of the bridge circuit. When the intensity of electric current is increased from zero, the full-scale output voltage is first increased. However, it has been discovered that the output voltage then decreases with increasing current intensity and equals zero as described later in a greater detail with reference to the accompanying drawings. At this point, the sensor becomes insensitive to any change in the mixture composition. As the current intensity is increased further, then the polarity of the output voltage is inverted.

During the course of investigation into this phenomenon, the present inventors has further discovered that, as the intensity of electric current is increased so that the temperature of the hot member is elevated, the rate of heat transfer through fuel vapor is increased to a proportionally larger degree than the increase in the rate of heat transfer through air, whereby the temperature difference between the hot member temperature as established with pure air and the hot member temperature as established with pure fuel vapor, on which difference the full-scale output potential of the bridge circuit is dependent, is decreased and even inverted.

The present inventors believe that this is due to the fact that, as the temperature of the hot member is raised, natural convection of gas begins to occur so that heat transfer is carried out by way of natural convection process in addition to thermal conduction process. At a certain point of temperature, natural convection will supersede thermal conduction in determining the amount of heat transfer per unit time so that the predominant mode of heat transfer will change from thermal conduction to natural convection. This temperature may be regarded as a transition point in the mode of heat transfer. It is presumed that, in situations where the natural convection is predominant, the kinematic viscosity of gases would prevail over the intrinsic thermal conductivity in governing the amount of heat transfer. As a result, although fuel vapor has a thermal conductivity smaller than that of air so that the amount of heat transfer by fuel vapor is smaller than the amount of heat transfer by air as long as the temperature of the hot member is low enough to permit thermal conduction to prevail, the amount of heat transfer by fuel vapor would surpass the amount of heat transfer by air if the hot member temperature is so high that natural convection prevails.

By limiting the electric current to such an intensity that heat transfer takes place primarily in the thermal conduction mode, a full-scale output signal having a high degree of reliability may be developed.

Preferably, the constant current supply circuit is adjusted such that electric current supplied to the hot member is of such an intensity that substantially corresponds to a point of transition at which, at the interface of the hot member and the mixture, the predominant mode of heat transfer changes from thermal conduction to natural convection.

With such adjustment, an output signal having as high voltage potential as possible is developed, yet avoiding or decreasing the undesirable effect of intake pressure variation.

These features of the invention as well as other features and advantages thereof will become apparent from the following description.

DESCRIPTION OF THE PREFERRED EMBODIMENTS

Figure 2:
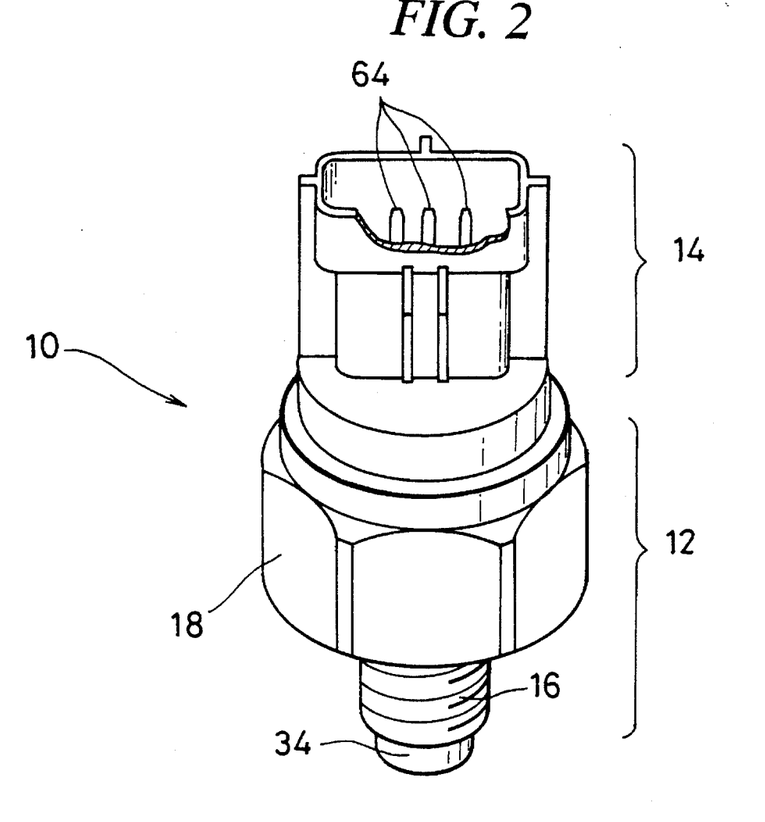
FIG. 2 is an enlarged perspective view, partly cut away, of the gas sensor according to the invention.
Figure 3:
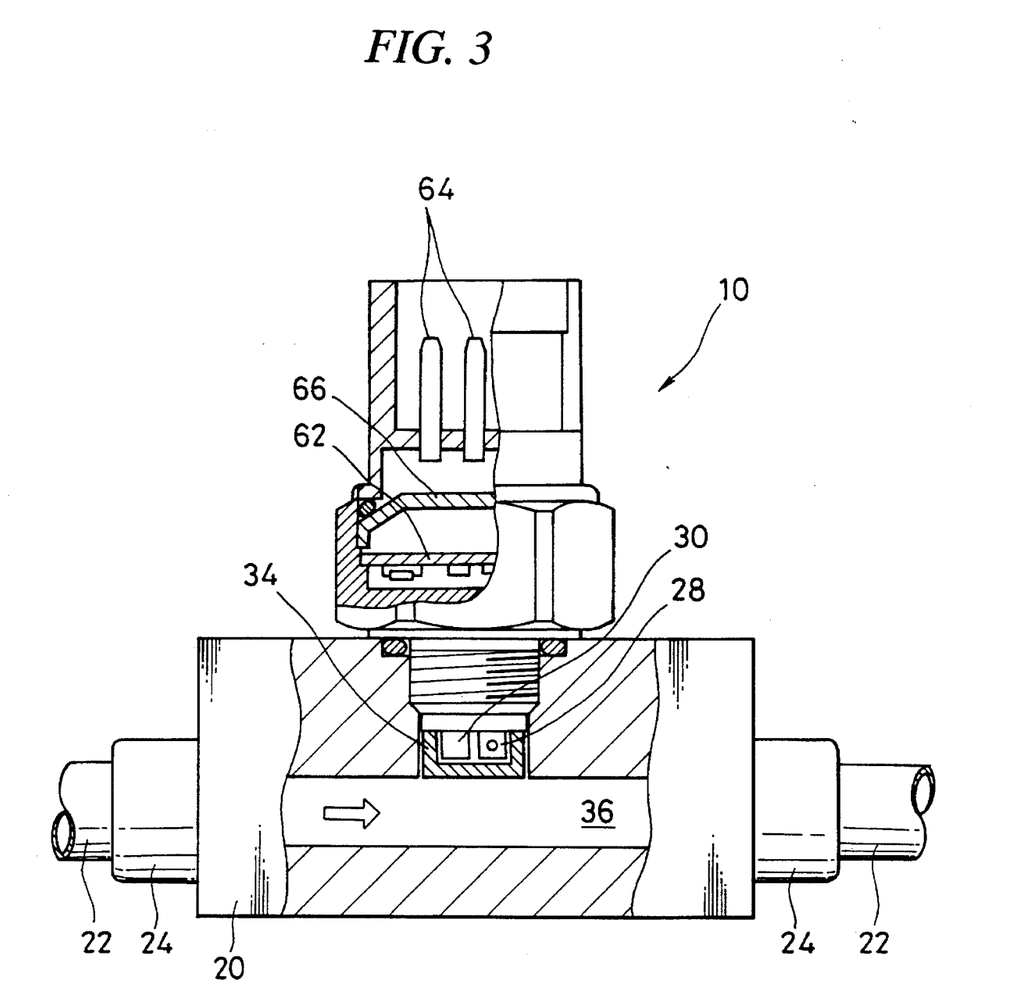
FIG. 3 is an enlarged side elevational view, partly cut away, of the gas sensor shown in FIG. 2 as fastened to a mounting block.

Referring to FIGS. 2 and 3, there is shown a gas sensor of the thermal conductivity type embodying the present invention. In the illustrated embodiment, the gas sensor 10 includes a metallic body section 12 and a electrical connector section 14 made of molded plastics and securely joined to the metal body 12. The metal body 12 has a threaded neck portion 16 and a hexagonal portion 18 adapted to be engaged by a wrench. As shown in FIG. 3, in use the sensor 10 may be screwed into a mounting fixture or adapter 20 suitably fixed on an automobile and connected to a purge line 22 by a pair of pipe couplings 24.

Figure 4:
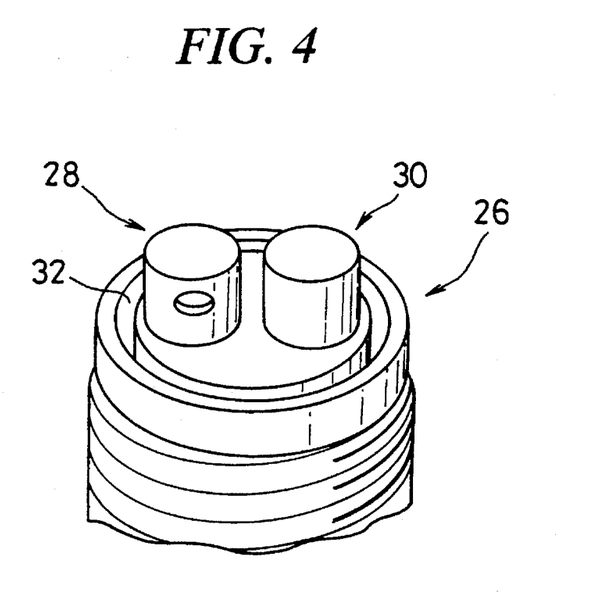
FIG. 4 is a perspective view, as viewed from below, of the head section of the gas sensor shown in FIG. 2.

As best shown in FIG. 4, the gas sensor 10 has a sensing head 26 provided with a sensing element 28 and a compensating element 30. The sensing head 26 is formed with an annular groove 32 in which a cap 34 made from porous sintered metal is press-fitted as shown in FIGS. 2 and 3. The cap 34 is primarily intended to serve as a flame-arresting screen. For this purpose, sintered metal forming the cap 34 preferably has a pore size of less than 100 micrometers.

Another important function of the porous cap 34 is to ensure that the sensing element 28 is sensitive only to the thermal conductivity of the fuel-air mixture to be tested, without undergoing any effect of gas velocity. To this end, the threaded portion 16 and the cap 34 as well as a passage 36 in the adapter 20 are so sized and arranged that the cap 34 and, hence, the sensing element 28 are offset from the flow of mixture. As a consequence, the fuel-air mixture flowing through the purge line will be brought into contact with the sensing element 28 solely by diffusion of gas.

Referring to FIGS. 5–8, the sensing element 28 comprises an electrically-heated hot member 38 which may be an electric heater of platinum wire or a thermistor. In order to improve the responsiveness of the sensor by making the thermal time constant of the hot member as small as possible, however, the hot member 38 is preferably made by the conventional micro-bridge fabrication process as disclosed in Japanese Patent Kokoku Publication No. 62-2438 and Japanese Patent Kokai Publication No. 2-170844.

Figure 6:
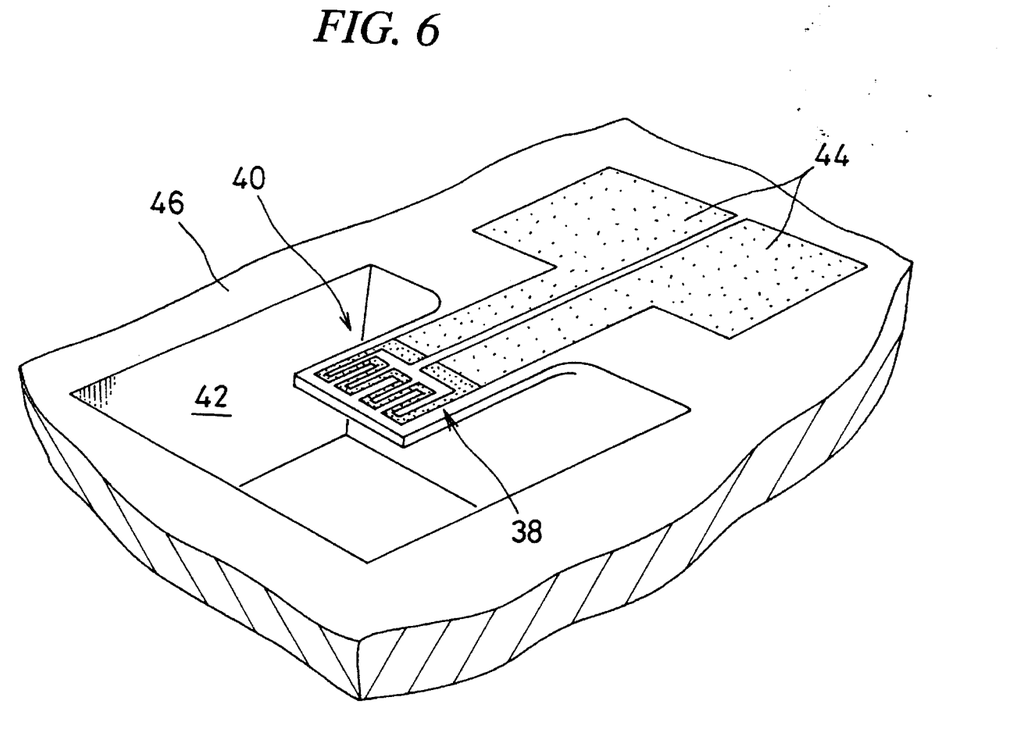
FIG. 6 is a perspective view, in a greatly enlarged scale, of a part of the sensing element shown in FIG. 5.
Figure 7:
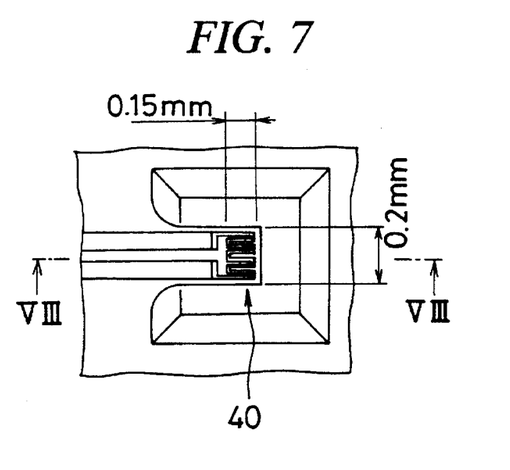
FIG. 7 is an enlarged top plan view of a part of the sensing element.
Figure 8:
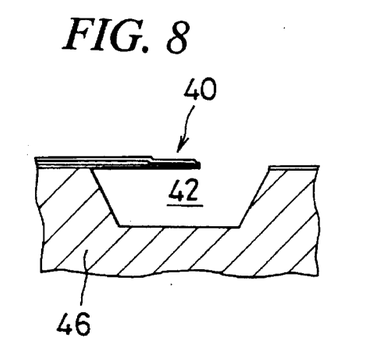
FIG. 8 is a cross-sectional view taken along the line VIII—VIII of FIG. 7.

To this end, an <100>-oriented single-crystal silicon wafer coated with a $SiO_2$ surface layer is processed by photoresist patterning and anisotropic etching techniques to form a micro-bridge structure 40 and an undercut cavity 42 as best shown in FIG. 6. The size of the undercut 42 may be 0.6 mm in length and width and 0.15 mm in depth. Then, a serrated pattern of a heater material, such as platinum or nickel, is deposited by sputtering on the surface of the micro-bridge to form the hot member 38. The size of the heater 38 on the micro-bridge structure 40 may be 0.2 mm by 0.15 mm as shown in FIG. 7. Thereafter, a pattern of an electrically conductive material such as gold is deposited similarly by sputtering to form a pair of electric terminals 44 in contact with the heater 38. The heater pattern 38 and the terminal pattern 44 are then coated by a $SiO_2$ layer and the wafer is cut into chip. The thickness of the heater 38 after $SiO_2$ coating may be in the order of 3.5 micrometers. The wafer chip 46 thus prepared is then fixed together with a pair of terminal pins 48 to a metal frame 50 by molding a glass potting 52. Finally, the terminals 44 are connected, respectively, by a bonding wire 54 of gold to associated terminal pins 48.

Figure 5:
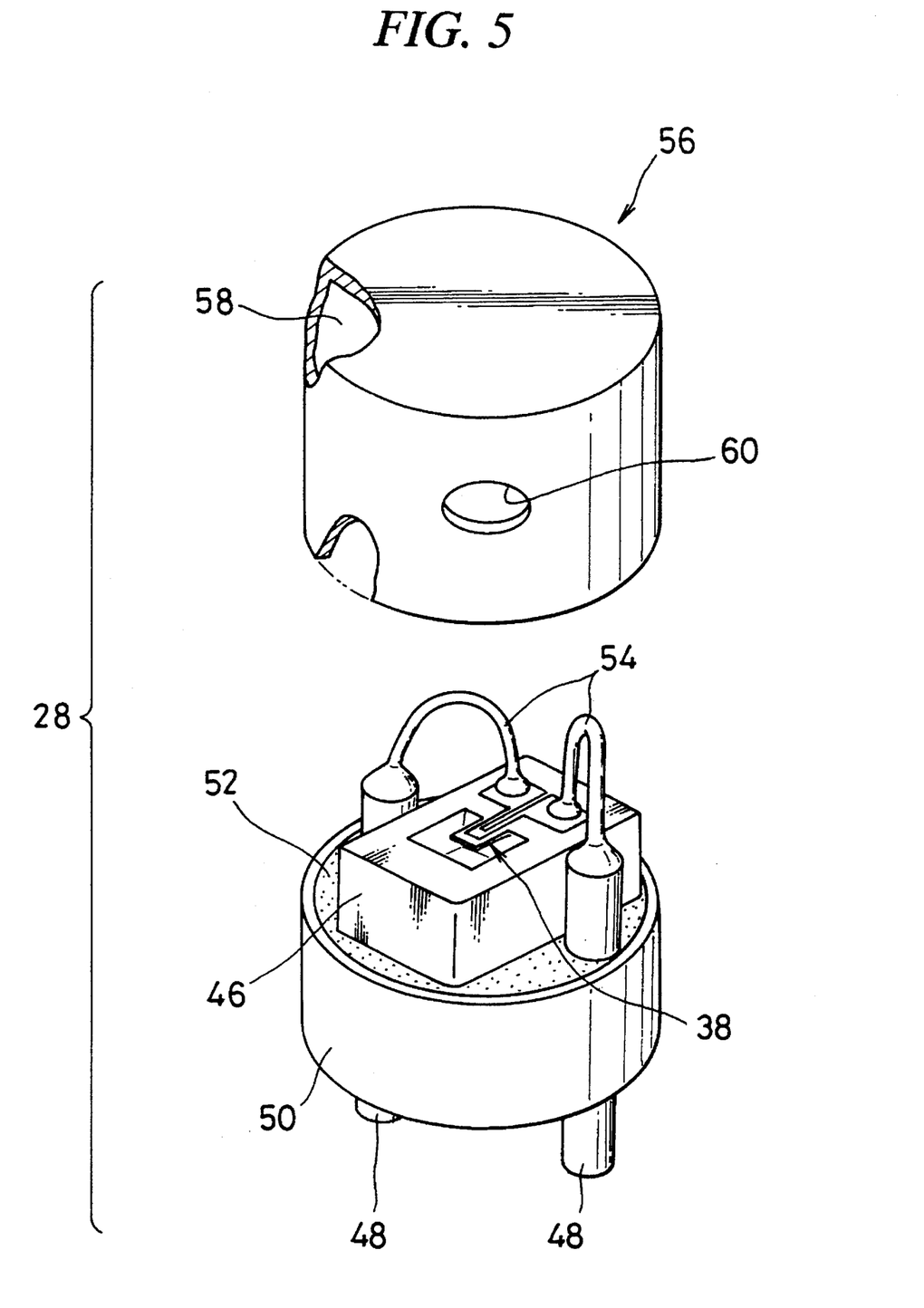
FIG. 5 is an enlarged perspective view, partly cut away, of the sensing element shown in FIG. 4, with a cap being shown as detached from a base.

The sensing element 28 also includes a metallic enclosure 56 which is tightly fitted over the metal frame 50 and which serves as a heatsink. The enclosure 56 defines a sensing chamber 58 therein and is provided with an opening 60 that communicates the sensing chamber with the surrounding atmosphere to allow the mixture to be tested to be brought in contact with the hot member 38.

The compensating element 30 is made identical in structure, size and thermal property to the sensing element 28, except that the enclosure of the compensating element 30 is not provided with an opening 60 and that the chamber therein is hermetically sealed and is filled with a reference gas which preferably is dry air under atmospheric pressure. Therefore, the compensating element 30 need not be described.

Figure 9:
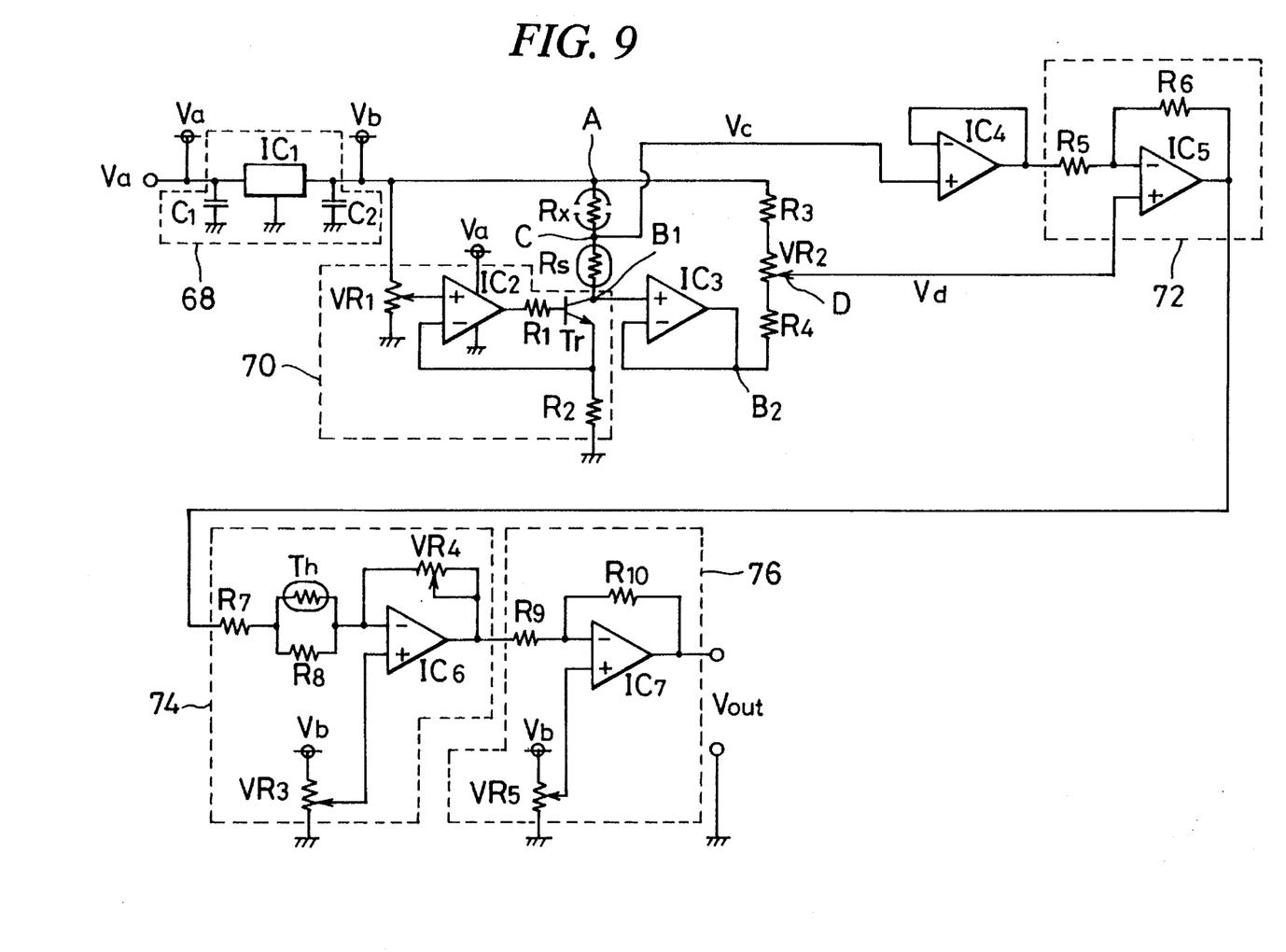
FIG. 9 is a wiring diagram of the electric circuit of the gas sensor shown in FIG. 2.

Referring again to FIGS. 2 and 3, the sensor 10 has a circuit board 62 on which an electric circuit comprising a Wheatstone bridge circuit, various amplifier circuits and other circuits described later with reference to FIG. 9 is provided. The electric circuit on the board 62 are connected to the sensing and compensating elements 28 and 30 as well as to three terminal pins 64. The circuit board 62 is protected by a partition 66 hermetically sealed to the metal body 12. As the electric circuit components of the gas sensor is provided in this manner on the circuit board 62 shielded within the metal body 12, the output signal of the sensor is free from any noise that may result from other electric components of the automobile.

Referring to FIG. 9 wherein the electric circuit of the gas sensor 10 is shown, the circuit may include a constant voltage circuit 68 for regulating the voltage $V_a$ from an external power source, such as DC12 V automobile batteries, to deliver a constant voltage $V_b$ of, for example, DC5 V. The constant voltage circuit 68 may be formed by a pair of capacitors $C_1$ and $C_2$ and a constant voltage regulator $IC_1$ which may be implemented by the integrated circuit "μPC78M05" marketed by NEC Corporation of Tokyo, Japan.

The regulated voltage $V_b$ is applied to the input terminals A of a four-resistor Wheatstone network comprising resistors $R_x$, $R_s$, $R_3$ and $R_4$. The hot member 38 of the sensing element 28 forms the resistor $R_x$ of the bridge circuit, with the hot member 38 of the compensating element 30 forming the resistor $R_s$.

The intensity of electric current flowing through the resistors $R_x$ and $R_s$, i.e., the hot members 38 of the sensing and compensating elements 28 and 30, is controlled by a constant current supply circuit 70 which may be comprised of a variable resistor $VR_1$, an operational amplifier $IC_2$, resistors $R_1$ and $R_2$, and a transistor Tr. The operational amplifier $IC_2$ as well as other operational amplifiers $IC_3$–$IC_7$ shown may be implemented by the integrated circuit "µPC452C" of NEC Corporation. The variable resistor $VR_1$ is adjusted in the manner described later with reference to FIGS. 10 and 11.

The bridge circuit may further include a variable resistor $VR_2$ for initial adjustment of the Wheatstone network such that the potential difference to be developed across the output terminals C and D when the hot member 38 of the sensing element 28 is in contact with air equals zero. Preferably, an operational amplifier $IC_3$ is connected between the resistors $R_s$ and $R_4$ so that the voltage potentials at the junctions $B_1$ and $B_2$ of the network become equal.

Upon application of voltage to the bridge circuit, the hot members or electric heaters 38 of the sensing and compensating elements 28 and 30 will be heated. The amount of heat generated in the hot members 38 equals $I^2R$. As the current intensity I is regulated constant by the constant current supply circuit 70 and since any change in the resistance $R_x$ of the hot member 38 of the sensing element 28 is negligible for the practical purposes, it can be regarded that heat generated in both of the hot members 38 is substantially equal. As the enclosures or heatsinks 56 of both elements are subjected to the identical ambient temperature, the temperature of the hot members 38 in a thermally equilibrated state will be dictated by the thermal conductivity of gas in respective chambers 58.

In this regard, it is essential that only the thermal conductivity of gas be reflected on the temperature of the hot member 38 of the sensing element 28. More specifically, an important prerequisite for measurement with a gas sensor of the thermal conductivity type is that transfer of heat from the hot member 38 to the heatsink 56 is performed without involving forced convection that would otherwise significantly affect the rate of heat transfer. It will be noted that, as the sensing element 28 is offset from the mixture passage 36 and is surrounded by the flame-arresting screen 34 so that the mixture is brought into contact with the sensing element 28 solely by diffusion, the hot member temperature is free from the effect of the gas velocity which may cause forced convection to occur.

Accordingly, any change in the fuel ratio in the fuel-air mixture to be tested will result in a change in the temperature of the hot member 38 of the sensing element 28, which change, in turn, results in a change in the electrical resistance $R_x$. Consequently, an unbalanced voltage potential representing the fuel ratio will be developed across the output terminals C and D of the Wheatstone bridge circuit.

Referring further to FIG. 9, the electric potentials $V_c$ and $V_d$ at the output terminals C and D of the bridge circuit are applied to a differential amplifier circuit 72 for amplification of the potential difference developed across the terminals C and D. Preferably, a buffer circuit $IC_4$ is arranged between the terminal C and the amplifier circuit 72 to avoid any effect that the electric current flowing through the circuit 72 may have upon the bridge circuit.

The output of the differential amplifier circuit 72 is further amplified by an inverting amplifier circuit 74 comprising an operational amplifier $IC_6$, resistors $R_7$ and $R_8$, a thermistor Th, and variable resistors $VR_3$ and $VR_4$. By properly selecting the constant of $R_7$, $R_8$, Th, and $VR_4$, the gain of the inverting amplifier circuit 74 may be afforded such a temperature dependency that the temperature dependency of the bridge circuit is canceled. Also, the variable resistor $VR_3$ is used to vary the temperature dependency of the inverting amplifier circuit 74 when the output voltage thereof is zero in such a manner as to cancel the temperature dependency of the bridge circuit when the unbalanced potential of the bridge is zero.

The output from the inverting amplifier circuit 74 is finally amplified by an inverting amplifier circuit 76 having an operational amplifier $IC_7$, resistors $R_9$ and $R_{10}$, and a variable resistor $VR_5$. By adjusting the variable resistor $VR_5$, the minimum voltage level of the final output when the voltage difference of the bridge circuit is zero may be set to a desirable value, for example, 1 V.

The concept of the present invention as well as the manner in which the variable resistor $VR_1$ of the constant current supply circuit 70 must be adjusted in accordance with the invention will be described with reference to the test results shown in FIGS. 10 and 11.

The present inventors have made and tested a prototype of the gas sensor 10 as shown in FIGS. 2–9 to see how the output voltage of the sensor as used for the measurement of fuel vapor content of a fuel-air mixture varies in response to varying current intensity I' and under different engine intake pressures.

Although air by itself is a two-component gas mixture consisting essentially of nitrogen gas and oxygen gas, it may be regarded as a single-component gas for the purposes of analysis since the thermal conductivity of air is definitely known as apparent from Table 1 and the ratio of nitrogen and oxygen in air is invariable. As a fuel-air mixture may therefore be considered as a two-component gas mixture consisting of air and fuel vapor, the thermal conductivity of the fuel-air mixture will reflect the fuel content. For the purposes of experiments, isobutane gas was used in place of fuel vapor since gasoline may conveniently be simulated by isobutane. It will be noted from Table 1 that the thermal conductivity of air is greater than that of isobutane.

The experiments were carried out under the standard atmospheric pressure (0 mmHg in gauge pressure) as well as under the vacuum of −500 mmHg (gauge pressure) which is often encountered in the engine intake system. The differential voltage U developed across the terminals C and D of the Wheatstone bridge was monitored as the current intensity I controlled by the constant current supply circuit 70 was varied from 0 to 20 mA by adjusting the variable resistor $VR_1$. The results are shown in the graph of FIG. 10.

Figure 10:
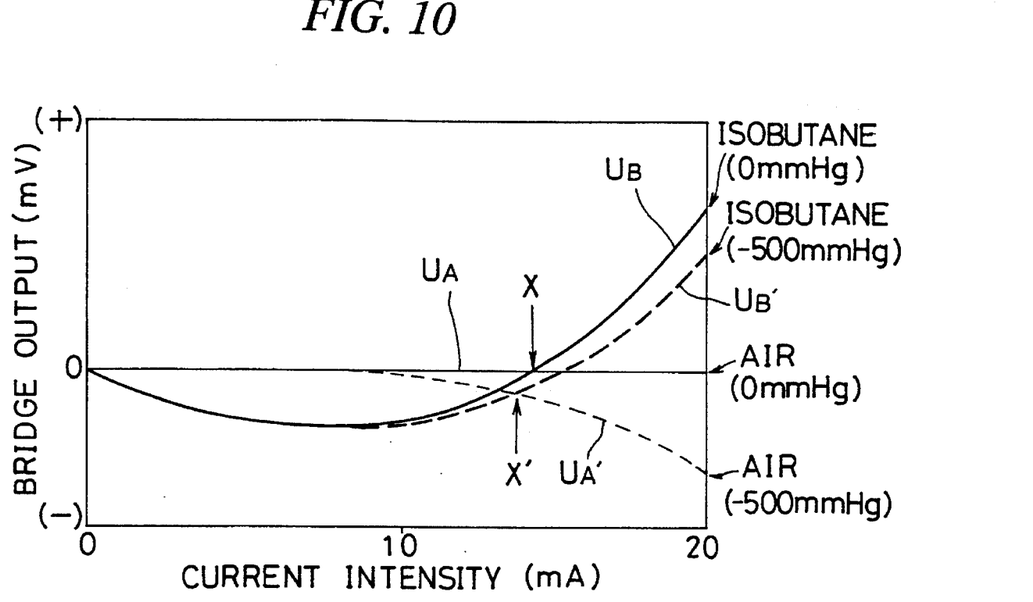
FIG. 10 is a graph showing the variation in the output of the bridge circuit resulting from a change in the supplied current intensity.

In the graph of FIG. 10, the line $U_A$ shown by the fine solid line and the curve $U_B$ shown by the bold solid line represents the variation in the output voltage U with pure air and pure isobutane, respectively, under 0 mmHg, with the curve $U_A'$ shown by the fine dotted line and the curve $U_B'$ shown by the bold dotted line showing the variation in the output voltage U with pure air and pure isobutane, respectively, under −500 mmHg. The curves $U_B$ and $U_B'$ represent the full-scale output of the bridge circuit under 0 mmHg and −500 mmHg, respectively.

It will be noted from the graph that, under the atmospheric pressure, the bridge output potential $U_A$ for air is constantly zero regardless of the variation in the current intensity. This is because both of the hot members 38 of the sensing and compensating elements 28 and 30 are subjected to the same condition of heat transfer so that the bridge circuit is balanced.

When tested with isobutane, the full-scale output $U_B$ increased with increasing current intensity. However, the bridge output $U_B$ culminated at about 8 mA and then decreased. Importantly, it has been discovered that, at point X of about 13–14 mA, the full-scale bridge output $U_B$ equals zero. After point X, the polarity of the bridge output $U_B$ was inverted and the potential level was increased with increasing current intensity.

It will also be noted that, under the negative pressure condition, the bridge output deviates with increasing current intensity, as shown by the dotted line curves $U_A'$ and $U_B'$. Under –500 mmHg, the curves $U_A'$ and $U_B'$ intersected with each other at point X'.

It will be understood that, at point X or X' the sensor will be insensitive to any change in the isobutane content. This point may be termed as the insensitive point. Obviously, the presence of such an insensitive point is most undesirable for a gas sensor.

Accordingly, upon discovery of the presence of the insensitive point, the present inventors have conducted a further experiment wherein the amount of heat transfer has been investigated in an attempt to clarify the reasons for the insensitivity. To this end, the gas sensor was operated with varying current intensity and the potential difference across the hot member 38 of the sensing element 28 was measured. Then the amount of heat Q generated in the hot member was calculated by multiplying the current intensity I by the potential difference V (Q=V·I). As, in a thermally equilibrated condition, the amount of generated heat Q is equal to the amount of transferred heat q transferred from the hot member to the surrounding heatsink (Q=q), the amount of generated heat Q as calculated was regarded as the amount of transferred heat q. The results are plotted in the graph of FIG. 11.

Figure 11:
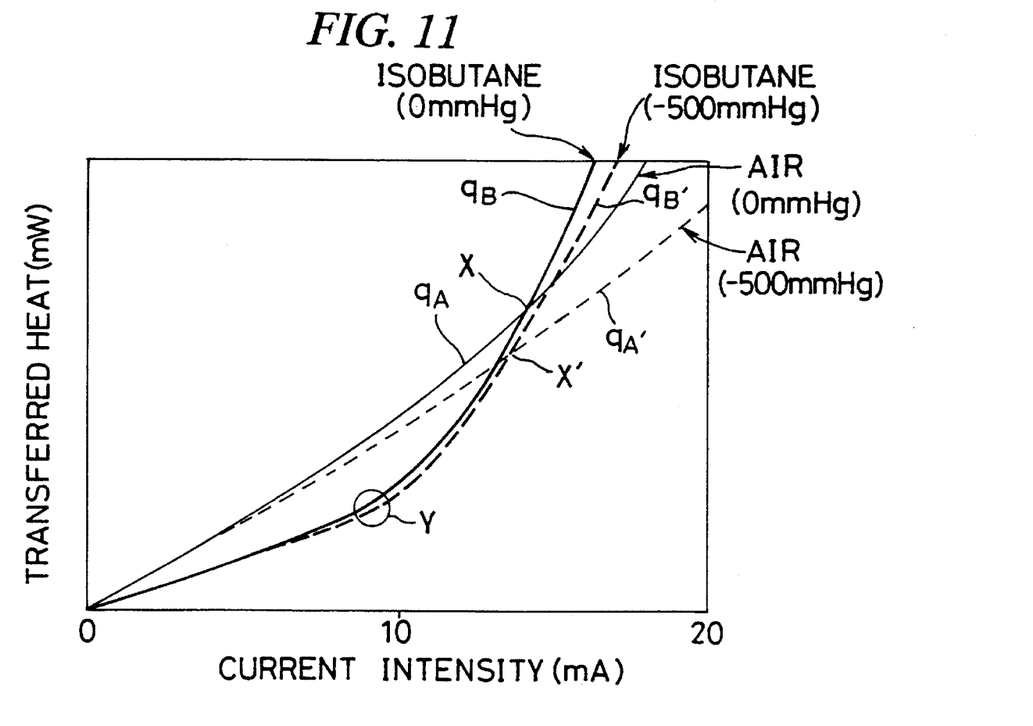
FIG. 11 is a graph showing the variation in the amount of heat transfer in response to a change in the electric current intensity.

In the graph of FIG. 11, the ordinate represents the amount of transferred heat q which is equal to the amount of generated heat Q as mentioned above. The curve $q_A$ shown by the fine solid line and the curve $q_B$ shown by the bold solid line represents the variation in the transferred heat q with pure air and pure isobutane, respectively, under 0 mmHg. The curve $q_A'$ shown by the fine dotted line and the curve $q_B'$ shown by the bold dotted line indicate the variation in the transferred heat q with pure air and pure isobutane, respectively, under –500 mmHg.

From the graph of FIG. 11, it will be noted that the amount of heat $q_A$ transferred by air increases fairly linearly with increasing current intensity. With regard to isobutane, the amount of transferred heat $q_B$ first increased roughly linearly in response to the increase in the current intensity. However, at point Y of the current intensity of about 8 mA, the inclination of the curve $q_B$ was changed and the amount of transferred heat $q_B$ increased steeply. Then the curves $q_A$ and $q_B$ crossed with each other at point X which corresponds to the insensitive point mentioned before.

It will be understood that the temperature of the hot member 38 of the compensating element 30 in the thermally equilibrated state is dependent on the amount of heat transfer $q_A$ by air and the hot member temperature of the sensing element 28 when contacted with pure isobutane is determined by the amount of heat transfer $q_B$. It will therefore be noted that the vertical distance between the curves $q_A$ and $q_B$ of FIG. 11 corresponds to the full-scale output $U_B$ shown in FIG. 10. The graph of FIG. 11 indicates that the amount of heat transfer $q_B$ by isobutane abruptly increases at transition point Y for some reason and this leads the curve $q_B$ to intersect with the curve $q_A$ thereby resulting in the insensitive point X or X'.

The present inventors believe that the occurrence of the transition point Y may be explained as follows.

Where the current intensity I is small so that the temperature of the hot member 38 is low, heat transfer from the hot member to the heatsink will be carried out solely by the thermal conduction process of gas, provided that there is no gas velocity. In the thermal conduction mode, the amount of transferred heat q per unit time may be expressed by the formula $$q \propto \lambda X (Th-Tg) \times C$$

wherein $\lambda$ is the thermal conductivity of gas, C being a constant, Th the temperature of the hot member, Tg the gas temperature. Given the electric current and, hence the amount of generated heat to be constant, then the amount of heat transfer and, hence, the hot member temperature Th will be governed solely by the thermal conductivity $\lambda$ of gas. It will be noted from Table 1 above that the thermal conductivity $\lambda$ of isobutane is smaller than that of air so that the amount of heat transfer by isobutane is smaller than that by air.

As the hot member temperature is raised by increasing the current intensity I, a mass of gas heated by the hot member will undergo natural convection so that heat transfer will be carried out in two ways; thermal conduction and natural convection. In the natural convection process, the amount of transferred heat q per unit time may be expressed by the formula $$q \propto \frac{\lambda}{\sqrt{v}} \times (Th - Tg) \times D$$

wherein $v$ is the kinematic viscosity of gas and D is a constant. Thus, the hot member temperature Th is affected not only by the thermal conductivity $\lambda$ of gas but also by the kinematic viscosity $v$. In the natural convection mode, the amount of heat transferred by isobutane is greater than that by air since the kinematic viscosity $v$ of isobutane is smaller than that of air.

Accordingly, although the amount of heat transfer by isobutane is smaller than that by air as long as the thermal conduction process prevails, the amount of heat transfer by isobutane will exceed the amount of heat transfer by air if the hot member temperature is high enough to permit natural convection to prevail. It is believed that, in the graph of FIG. 11, a transition in the predominant mode of heat transfer from thermal conduction to natural convection takes place at the point Y.

It will be noted from FIGS. 10 and 11 that, at around the transition point Y, a full-scale output potential of a maximum level is obtainable. Therefore, according to the present invention, the variable resistor $VR_1$ of the constant current supply circuit 70 is adjusted such that the current intensity I which substantially corresponds to the transition point Y is supplied to the hot members.

One convenient way to achieve this is to first detect the insensitive point X and then to find the transition point Y. By way of approximation, the desired current intensity may be sought, for example, by bisecting the current intensity that corresponds to the insensitive point X.

Figure 12:
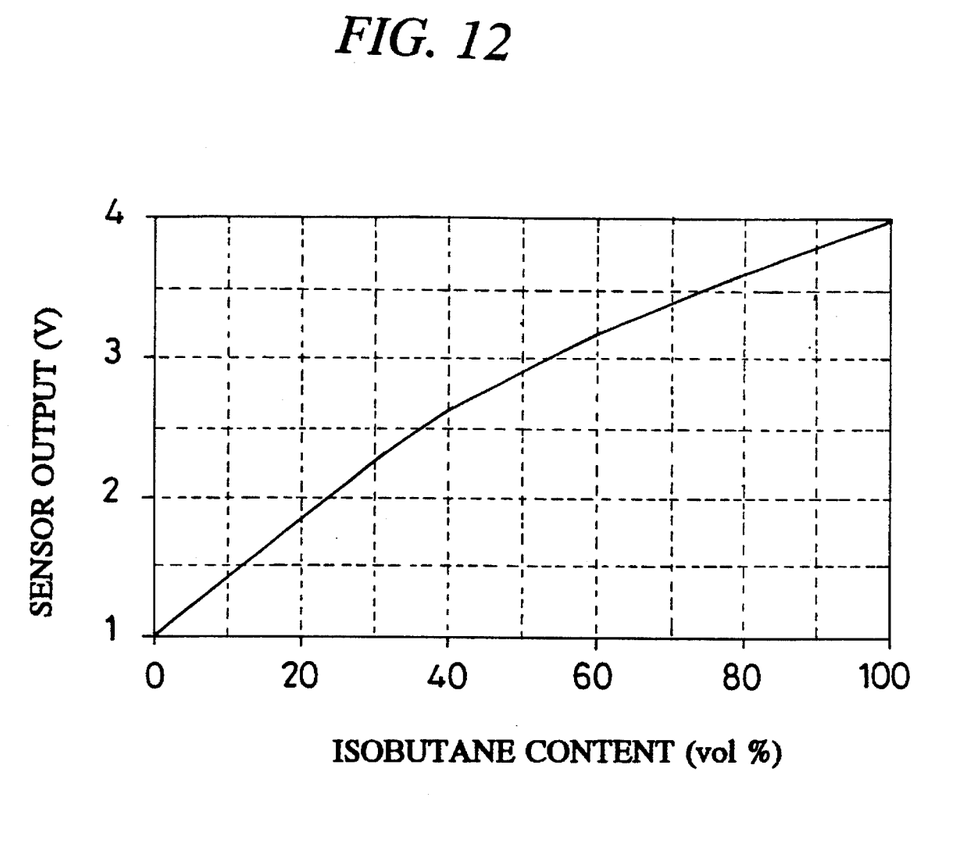
FIG. 12 is a graph showing the final output voltage of the gas sensor according to the invention.

FIG. 12 indicates the final output voltage of the inverting amplifier circuit 76 of the prototype as issued for varying isobutane content when the hot members are heated with a current intensity of about 8 mA according to the invention. It will be noted that a fairly good correlation is found between the sensor output and the isobutane content.

The prototype gas sensor was tested under varying gas pressure to verify the effect of pressure variation upon the output voltage. The prototype was operated with different current intensity and the output of the sensor under varying pressure was measured. Then the rate of fluctuation in the output potential as compared with the output as measured with air under the standard atmospheric pressure was computed. The results are plotted in the graphs of FIGS. 13 and 14 wherein the abscissa indicates the gas pressure and the ordinate represents the rate of fluctuation in the final output potential. The graphs of FIGS. 13 and 14 show the results when the prototype was operated with a current intensity of about 8 mA and 16–17 mA, respectively.

Figure 13:
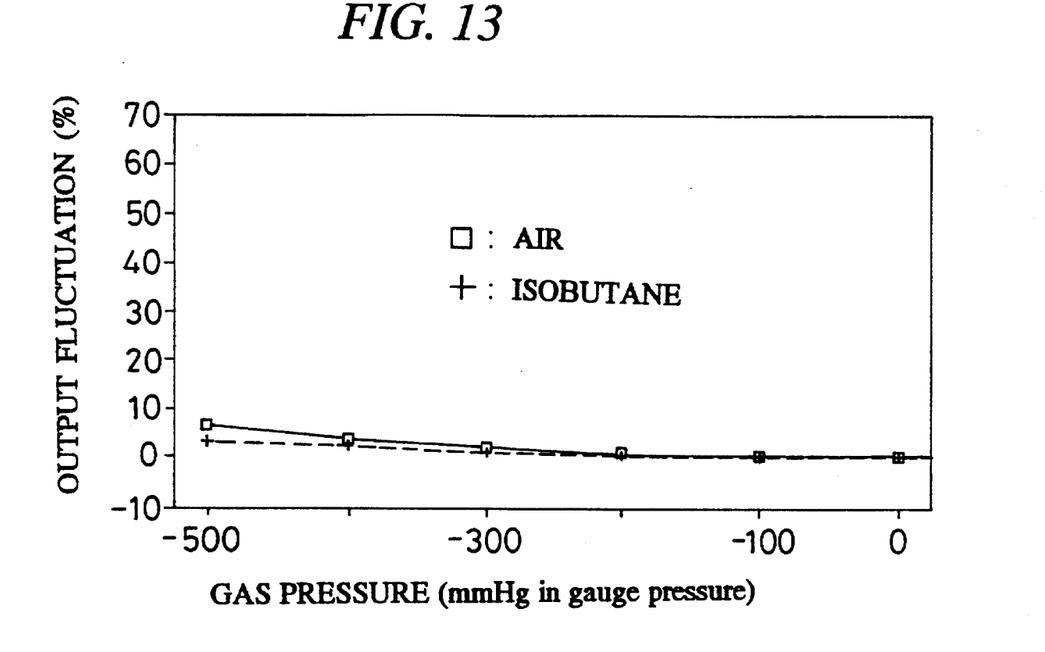
FIGS. 13 and 14 are graphs showing the output voltage fluctuation under varying gas pressure when the gas sensor was operated with a current intensity of about 8 mA and 16–17 mA, respectively.
Figure 14:
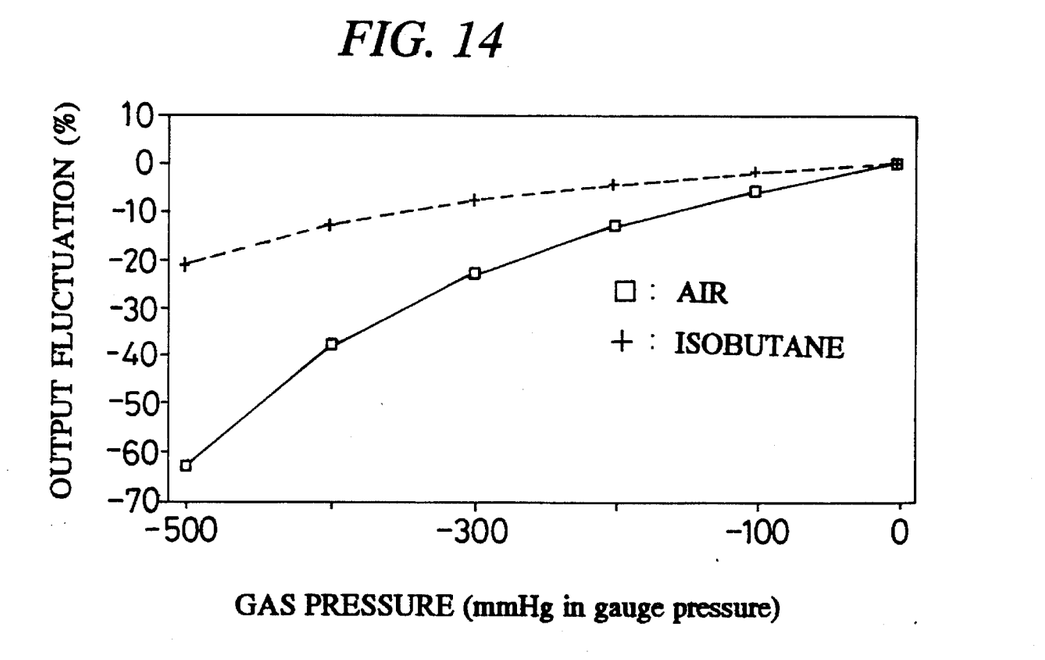

It will be noted from the graph of FIG. 13 that, when the hot members were heated with a current intensity of about 8 mA according to the invention, the fluctuation in the full-scale output was less than about 5%. In contrast, when the sensor was operated with a current intensity of about 16–17 mA, the output fluctuation was prohibitive as apparent from the graph of FIG. 14.

Figure 15:
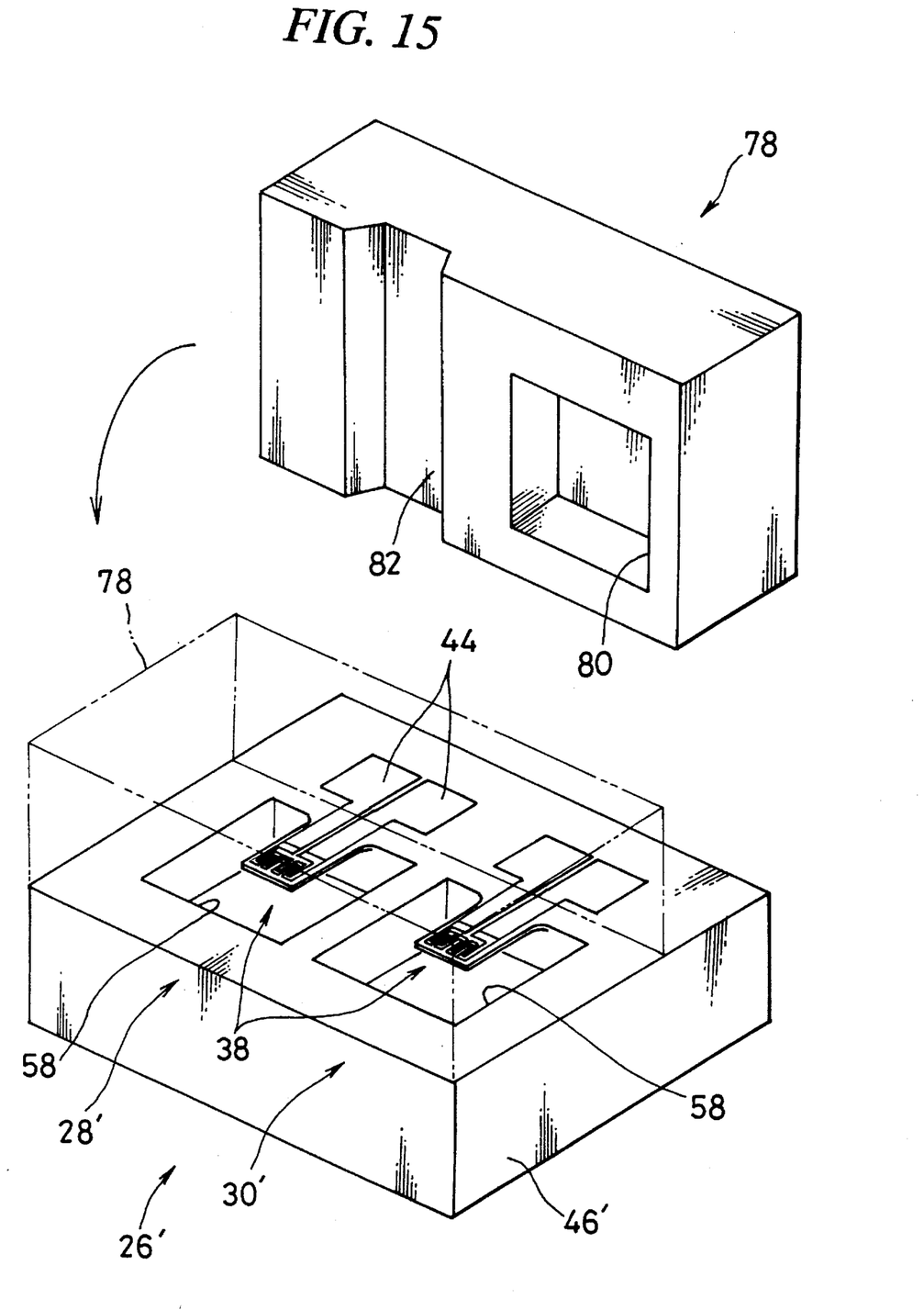
FIG. 15 is a perspective view of a modified form of the sensor head.

FIG. 15 illustrates a modified form of the sensor head of the gas sensor 10. Parts and members similar to those of the foregoing embodiment are designated by like reference numerals suffixed by a prime and will not be described again. To describe only the difference, the hot members 38 of the sensing and compensating elements 28' and 30' are formed in the similar manner but are integrated on a common silicon wafer chip 46'. A heatsink structure 78 is used to define the reference and sensing chambers in combination with the chip 46'. To this end, the heatsink structure 78 is processed similarly by the anisotropic etching of a single-crystal silicon wafer to form a cavity 80 and a channel 82. The depth of the cavity 80 and the channel 82 is less than ¼ of the width of the hot members 38, preferably less than 0.05 mm.

The heatsink structure 78 is firmly bonded to the chip 46' as shown by the ghost line to form the sensing head 26'. The reference chamber 58 of the compensating element 30' is filled with a reference gas such as dry air under the atmospheric pressure in a manner similar to the first embodiment. The sensing chamber 58 of the sensing element 28' is in communication with the gas to be tested via the channel 82. The electric terminals 44 of the elements may be connected to terminal pins, not shown, in a manner similar to the foregoing embodiment by the conventional wire bonding technique. The sensing head 26' as assembled may be similarly enclosed by the flame-arresting screen 34.

Figure 16:
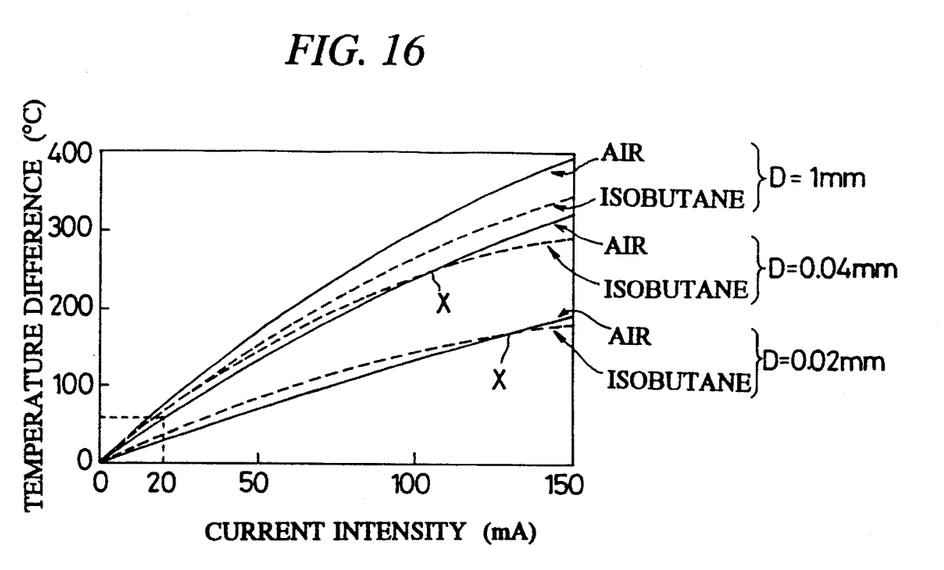
FIG. 16 is a graph showing the variation in the temperature difference between the temperature of the hot member of the sensing element and the ambient temperature as computed for varying current intensity and different heatsink distance; and, FIG. 17 is a graph showing in an enlarged scale the dotted area shown in the graph of FIG. 16.
Figure 17:
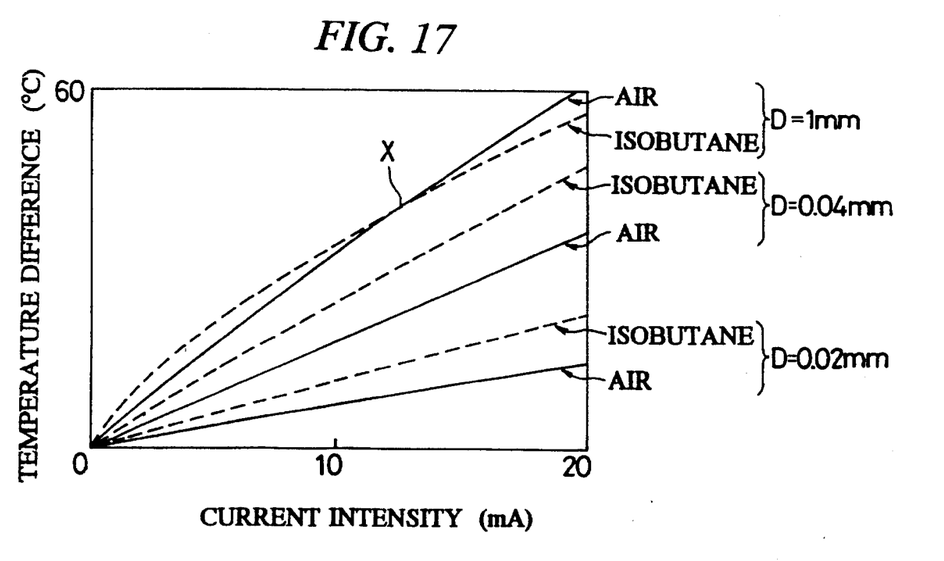

One of the advantages of the modified arrangement is that the manufacturing process is much simplified. Another advantage of the modified embodiment is that the level of the output voltage of the gas sensor is considerably improved because of the short distance between the hot members 38 and the opposite surface of the heatsink 78. The present inventors have calculated by simulation the temperature difference between the temperature of the hot member 38 of the sensing element 28' and the ambient temperature to be attained at varying current intensity when the distance D between the hot members 38 and the opposite surface of the heatsink 78 is 1 mm, 0.04 mm and 0.02 mm, respectively. The results are shown in the graphs of FIGS. 16 and 17.

It will be noted from these graphs that, when the distance D is reduced to 0.04 mm, the current intensity at which the insensitive point X occurs is about 110 mA so that the hot member of the sensing element can advantageously be heated with an increased current intensity of about 60 mA, in contrast to 8 mA which is possible where the distance D is 1 mm. Also, when the distance D is about 0.02 mm, the current intensity at which the insensitive point X occurs is about 130 mA so that the current intensity may be increased to about 70 mA. In this manner, the smaller the distance D is, the greater is the current intensity at which the insensitive point X occurs. Accordingly, by reducing the distance D, the hot members of the sensing and compensating elements can be heated with an increased current intensity whereby the magnitude of the output voltage as well as the sensitivity of the sensor are increased.

While the present invention has been described herein with reference to the specific embodiments thereof, it is contemplated that the invention is not limited thereby and various modifications and alterations may be made therein without departing from the scope of the invention. In particular, the gas sensor of the invention has been described as being suitable for the measurement of the fuel vapor content in a fuel-air mixture. However, the sensor may equally be applied to the measurement of any gas mixture consisting of a first component and a second component which has a smaller thermal conductivity and a smaller kinematic viscosity than those of the first component.

What is claimed is:

1. A gas sensor of the thermal conductivity type for use in measuring a fuel vapor content of a mixture of air and fuel vapor, said sensor comprising:

a body;

a sensing element and a compensating element mounted on said body and adapted to be brought in contact with the mixture to be tested;

said sensing element having a first enclosure defining a sensing chamber and a first electric heater disposed in said sensing chamber;

said compensating element having a second enclosure defining a reference chamber and a second electric heater disposed in said reference chamber;

said first and second heaters being substantially identical in thermal property with each other and being made of a material having an electrical resistance that varies with temperature;

said second enclosure being hermetically sealed and filled with a reference gas under a predetermined pressure to hold said second heater in contact with said reference gas, whereby the temperature of said second heater when operated is dictated by the thermal conductivity of said reference gas;

said first enclosure being apertured to permit said mixture to be brought in contact with said first heater, whereby the temperature of said first heater when operated is dictated by the thermal conductivity of said mixture;

a four-resistor Wheatstone bridge circuit mounted on said body and having two input terminals and two output terminals;

said first and second heaters forming two resistors of said bridge circuit so that an unbalanced potential is developed across said output terminals in response to a change in the electrical resistance of said first and second heaters caused by a change in the temperature thereof;

means for applying an electric potential across said input terminals of said bridge circuit;

current control means for controlling electric current flowing through said first and second heaters at such a constant intensity that generally corresponds to a point of transition at which, at the interface of said first heater and said mixture, the predominant mode of heat transfer from said first heater to said mixture changes from thermal conduction to convection;

output means for delivering said unbalanced potential developed across said output terminals; and wherein said first and second heaters of said sensing and compensating elements are formed on a single substrate and wherein said first and second enclosures are formed in part by a single heatsink secured to said substrate.

2. A gas sensor according to claim 1, wherein each of said substrate and heatsink is made from a single crystal silicon wafer.

3. A gas sensor according to claim 1, further comprising a flame-arresting screen enclosing said sensing and compensating elements.

4. A gas sensor according to claim 3, wherein said body is adapted to be mounted to a conduit for a mixture to be tested and wherein said flame-arresting screen is so positioned and sized that said sensing and compensating elements are offset from the flow of mixture flowing through said conduit.

5. A method of adjusting a gas sensor of the thermal conductivity type for use in measuring a fuel vapor content of a mixture of air and fuel vapor, said sensor having a Wheatstone bridge circuit with two input terminals and two output terminals, a sensing element having an electrically-heated first member which in use is brought in contact with the mixture to be tested, a compensating element having an electrically-heated second member in contact with a reference gas, said electrically-heated members being made of a material having an electrical resistance that varies with temperature, said first member forming an arm of said bridge circuit, said second member forming another arm of said bridge circuit, and a constant current supply circuit for supplying a constant electric current across said input terminals of said bridge circuit, said method comprising the steps of:

bringing said first member in contact with a mixture of air and fuel vapor having a predetermined fuel content;

supplying an electric current of varying intensity across said input terminals of said bridge circuit thereby to heat said first and second members;

monitoring the voltage potential developed across said output terminals of said bridge circuit;

detecting the magnitude of electric current intensity at which the voltage potential equals zero; and, adjusting said constant current supply circuit in such a manner that an electric current of a predetermined constant intensity which is roughly equal to a half of said magnitude is supplied to said first and second members.

* * * * *